(12) United States Patent
Nogueira et al.

(10) Patent No.: US 11,564,617 B2
(45) Date of Patent: Jan. 31, 2023

(54) SEIZURE PREDICTION BASED ON COMPARISON OF BIOLOGICAL INFORMATION ACROSS WAKE AND SLEEP PERIODS

(71) Applicant: Children's Medical Center Corporation, Boston, MA (US)

(72) Inventors: Adriano Nogueira, Sao Paulo (BR); Tobias Loddenkemper, Natick, MA (US)

(73) Assignee: Children's Medical Center Corporation, Boston, MA (US)

( * ) Notice: Subject to any disclaimer, the term of this patent is extended or adjusted under 35 U.S.C. 154(b) by 372 days.

(21) Appl. No.: 15/742,082

(22) PCT Filed: Jul. 6, 2016

(86) PCT No.: PCT/US2016/041085
§ 371 (c)(1),
(2) Date: Jan. 5, 2018

(87) PCT Pub. No.: WO2017/007808
PCT Pub. Date: Jan. 12, 2017

(65) Prior Publication Data
US 2018/0206776 A1  Jul. 26, 2018

Related U.S. Application Data

(60) Provisional application No. 62/205,505, filed on Aug. 14, 2015, provisional application No. 62/189,093, filed on Jul. 6, 2015.

(51) Int. Cl.
*A61B 5/01*   (2006.01)
*G16H 50/30*   (2018.01)
(Continued)

(52) U.S. Cl.
CPC .............. *A61B 5/4094* (2013.01); *A61B 5/01* (2013.01); *A61B 5/7275* (2013.01); *G16H 20/00* (2018.01);
(Continued)

(58) Field of Classification Search
CPC ....... A61B 5/4094; A61B 5/01; A61B 5/7275; A61B 5/02055; G16H 20/00; G16H 50/30
See application file for complete search history.

(56) References Cited

U.S. PATENT DOCUMENTS 4,453,551 A  *  6/1984  Anderson .............. A61B 5/046
                                                 600/517
4,545,388 A  *  10/1985  John .................... A61B 5/0484
                                                 600/544
(Continued)

OTHER PUBLICATIONS

Stuijvenberg, M. V., Steyerberg, E. W., Derksen-Lubsen, G., & Moll, H. A. (1998). Temperature, Age, and Recurrence of Febrile Seizure. Archives of Pediatrics & Adolescent Medicine, 152(12). doi: 10.1001/archpedi.152.12.1170 (Year: 1998).*
(Continued)

*Primary Examiner* — David J. McCrosky
(74) *Attorney, Agent, or Firm* — Melissa Hunter-Ensor; Kristopher Reichlen; Greenberg Traurig, LLP

(57) ABSTRACT

An apparatus for generating a prediction that a patient will experience a seizure by monitoring a patient's body temperature over time is provided. The apparatus may include a sensor to sense temperature. The apparatus may monitor, using the sensor, the body temperature of the patient and compare the body temperature over a first period of time and a second period of time. The apparatus may generate a prediction of whether the patient will experience a seizure following the second period of time based at least in part on a result of the comparing.

20 Claims, 8 Drawing Sheets

(51) Int. Cl.
  *A61B 5/00*    (2006.01)
  *G16H 20/00*   (2018.01)
  *A61B 5/0205*  (2006.01)
  *A61B 5/11*    (2006.01)

(52) U.S. Cl.
  CPC .......... *G16H 50/30* (2018.01); *A61B 5/02055* (2013.01); *A61B 5/1118* (2013.01)

(56) References Cited

U.S. PATENT DOCUMENTS

| | | | |
|---|---|---|---|
| 6,304,775 B1 | 10/2001 | Iasemidis et al. | |
| 7,269,455 B2 | 9/2007 | Pineda | |
| 7,285,090 B2* | 10/2007 | Stivoric | A61B 5/743 600/300 |
| 7,630,757 B2* | 12/2009 | Dorfmeister | A61B 5/048 600/407 |
| 8,140,143 B2 | 3/2012 | Picard et al. | |
| 8,795,173 B2 | 8/2014 | Poh et al. | |
| 2005/0107655 A1 | 5/2005 | Holzner | |
| 2006/0129202 A1 | 6/2006 | Armstrong | |
| 2006/0265022 A1* | 11/2006 | John | A61B 5/02 607/45 |
| 2008/0161707 A1* | 7/2008 | Farringdon | A61B 5/04012 600/509 |
| 2008/0161715 A1* | 7/2008 | Stivoric | G16H 40/63 600/549 |
| 2009/0177068 A1* | 7/2009 | Stivoric | A61B 5/01 600/365 |
| 2010/0268056 A1 | 10/2010 | Picard et al. | |
| 2010/0280334 A1 | 11/2010 | Carlson et al. | |
| 2010/0280335 A1 | 11/2010 | Carlson et al. | |
| 2011/0004072 A1* | 1/2011 | Fletcher | A61B 5/6807 600/300 |
| 2011/0306846 A1 | 12/2011 | Osorio | |
| 2012/0296175 A1* | 11/2012 | Poh | A61B 5/02405 600/301 |
| 2013/0060167 A1* | 3/2013 | Dracup | A61B 5/11 600/595 |
| 2013/0080185 A1* | 3/2013 | Picard | A61B 5/0022 705/2 |
| 2013/0096391 A1* | 4/2013 | Osorio | A61B 5/165 600/301 |
| 2013/0096393 A1* | 4/2013 | Osorio | A61B 5/048 600/301 |
| 2015/0031964 A1* | 1/2015 | Bly | A61B 5/7465 600/301 |

OTHER PUBLICATIONS wikipedia.com, Standard Deviation, Jul. 20, 2014, https://web.archive.org/web/20140720010209/https://en.wikipedia.org/wiki/Standard_deviation (Year: 2014).*
Poh, M.-Z. (2011). Continuous assessment of epileptic seizures with wrist-worn biosensors. (Year: 2011).*
Foldvary-Schaefer, N., 2021. Sleep and Epilepsy, [online] ResearchGate. Available at: <https://www.researchgate.net/profile/Madeleine_Grigg-Damberger/publication/26800739_Sleep_and_Epilepsy/links/5437cbc30cf2027cbb204811/Sleep-and-Epilepsy.pdf> [Accessed May 19, 2021], (Year: 2009).*
Hayes, T., Digital Trends, "What's inside a fitness tracker, anyway?" Nov. 29, 2014. <https://www.digitaltrends.com/wearables/whats-inside-fitness-tracker-anyway/> (Year: 2014).*
PCT/US2016/041085, Oct. 7, 2016, International Search Report and Written Opinion.
PCT/US2016/041085, Jan. 18, 2018, International Preliminary Report on Patentability.
International Search Report and Written Opinion dated Oct. 7, 2016 for Application No. PCT/US2016/041085.
International Preliminary Report on Patentability dated Jan. 18, 2018 for Application No. PCT/US2016/041085.
[No Author Listed] E4 Wristband. Last accessed Apr. 9, 2015 at https://www.empatica.com/product-e4. 7 pages.
Collins, Epilepsy research benefits from the crowd. http://directorsblog.nih.gov/2015/01/20/epilepsy-research-benefits-from-the-crowd/ . Posted Jan. 20, 2015.
Golestani et al., Can we predict the unpredictable? Oct. 30, 2014;4:6834. doi: 10.1038/srep06834.
Haut et al., Modeling seizure self-prediction: an e-diary study. Epilepsia. Nov. 2013;54(11):1960-7. doi: 10.1111/epi.12355. Epub Sep. 20, 2013.
Hofstra et al., The circadian rhythm and its interaction with human epilepsy: a review of literature. Sleep Med Rev. Dec. 2009;13(6):413-20. doi: 10.1016/j.smrv.2009.01.002. Epub Apr. 24, 2009.
Martinez-Nicolas et al., Uncovering different masking factors on wrist skin temperature rhythm in free-living subjects. PLoS One. 2013;8(4):e61142. doi: 10.1371/journal.pone.0061142. Epub Apr. 5, 2013.
Nogueira Existence of a potential neurogenic system in the adult human brain. J Transl Med. Mar. 22, 2014;12:75. doi: 10.1186/1479-5876-12-75.
Ramgopal et al., Seizure detection, seizure prediction, and closed-loop warning systems in epilepsy. Epilepsy Behav. Aug. 2014;37:291-307. doi: 10.1016/j.yebeh.2014.06.023. Epub Aug. 29, 2014.
Poh et al., "Convulsive seizure detection using a wrist-worn electrodermal activity and accelerometry biosensor," Epilepsia, 2012, vol. 53, No. 5, pp. e93-e97.

\* cited by examiner

SEIZURE PREDICTION BASED ON COMPARISON OF BIOLOGICAL INFORMATION ACROSS WAKE AND SLEEP PERIODS

RELATED APPLICATIONS

The present application is a national stage filing under 35 U.S.C. § 371 of International Application No. PCT/US2016/041085, filed Jul. 6, 2016, which claims priority under 35 U.S.C. § 119(e) to U.S. Provisional Application No. 62/205,505, filed Aug. 14, 2015 and to U.S. Provisional Application No. 62/189,093, filed Jul. 6, 2015, each of which is herein incorporated by reference in its entirety.

BACKGROUND

Epilepsy often leads to a poor quality of life for patients in part because seizures cannot be reliably predicted and, in extreme cases, are associated with sudden unexpected death in epilepsy (SUDEP).

Existing methods to predict seizures focus principally on analysis of brain electrical activity by electroencephalogram (EEG) or invasive monitoring.

SUMMARY

In one embodiment, there is provided a system useful for predicting occurrence of seizures in a monitored individual. The system comprises a computer store containing data defining at least one biological characteristic of the monitored individual, wherein the data defining at least one biological characteristic of the monitored individual comprises first data for a first time period and second data for a second time period, wherein the first time period is a wake period for the monitored individual and the second time period is a sleep period for the monitored individual, and wherein the at least one biological characteristic comprises a body temperature of the monitored individual. The system further comprises a computer server coupled to the computer store and programmed to determine at least one first statistical value relating to the first data for the first time period defining the at least one biological characteristic for the first time period, wherein the at least one first statistical value comprises a first average body temperature of the monitored individual in the wake period, and to determine at least one second statistical value relating to the second data for the second time period defining the at least one biological characteristic for the second time period, wherein the at least one second statistical value comprises a second average body temperature of the monitored individual in the sleep period. The computer server is further programmed to compare the first average body temperature to the second average body temperature, and, based on a result of the comparing, output a prediction of whether the monitored individual will experience a seizure during a third time period following the second time period, wherein the third time period is a wake period of the monitored individual following the sleep period.

In another embodiment, there is provided a system to predict occurrence of a seizure in a monitored individual. The system comprises a wrist device arranged to be worn on a wrist of the monitored individual, wherein the wrist device comprises an accelerometer to measure a movement of the wrist of the monitored individual, a temperature sensor to sense a temperature of the wrist of the monitored individual, and an electrodermal activity (EDA) sensor to sense an EDA of the wrist of the monitored individual. The wrist device further comprises a user interface to output diagnostic information for the monitored individual. The system further comprises at least one processor and at least one storage medium having encoded thereon executable instructions that, when executed by the at least one processor, cause the at least one processor to carry out a method. The method comprises determining, based on acceleration data for the wrist of the monitored individual collected by the accelerometer, a wake period for the monitored individual during which the monitored individual is awake, monitoring, using the temperature sensor and during the wake period, a first body temperature of the wrist of the monitored individual over the wake period, monitoring, using the EDA sensor and during the wake period, a first EDA of the wrist of the monitored individual over the wake period, determining, based on acceleration data for the wrist of the monitored individual collected by the accelerometer, a sleep period for the monitored individual during which the monitored individual is asleep, monitoring, using the temperature sensor and during the sleep period, a second body temperature of the wrist of the monitored individual over the sleep period, monitoring, using the EDA sensor and during the sleep period, a second EDA of the wrist of the monitored individual over the wake period, comparing the first body temperature and the first EDA of the wrist for the wake period to the second body temperature and second EDA of the wrist for the sleep period, generating a prediction of whether the patient will experience a seizure during a wake period following the sleep period based at least in part on a result of the comparing, and triggering output of the prediction via the user interface of the wrist device.

In a further embodiment, there is provided an apparatus comprising at least one first sensor to sense temperature, at least one processor, and at least one storage having encoded thereon executable instructions that, when executed by the at least one processor, cause the at least one processor to perform a method. The method comprises monitoring, using the at least one first sensor and during a first period of time, a first body temperature of a patient over the first period of time, monitoring, using the at least one first sensor and during a second period of time following the first period of time, a second body temperature of the patient over the second period of time, comparing the first body temperature of the patient of the first period of time to the second body temperature of the patient over the second period of time, and generating a prediction of whether the patient will experience a seizure following the second period of time based at least in part on a result of the comparing.

In another embodiment, there is provided a method comprising comparing a first body temperature of a patient over a first period of time to a second body temperature of the patient over a second period of time following the first period of time and generating a prediction of whether the patient will experience a seizure following the second period of time based at least in part on a result of the comparing.

In a further embodiment, there is provided at least one non-transitory storage medium encoded with executable instructions that, when executed by at least one processor, cause the at least one processor to carry out a method of analyzing data relating at least to a first biological characteristic of a patient over a first wake period and a first sleep period that immediately follows the first wake period, wherein the patient is awake during the first wake period and the patient is asleep during the first sleep period. The method comprises comparing first data on the first biological characteristic of the patient for the first wake period to second data on the first biological characteristic of the patient over the first sleep period and generating, based at least in part on a result of the comparing, a prediction of whether the patient will experience a seizure during a second wake period that immediately follows the first sleep period.

In one embodiment, there is provided a system to predict occurrence of seizure through analysis of at least one biological parameter in function of at least one period of circadian rhythm. Seizure prediction may be assessed by, for example, a ratio between mean skin temperature during a sleep period and mean skin temperature during a wake period preceding the sleep period.

The foregoing summary is to be considered non-limiting.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
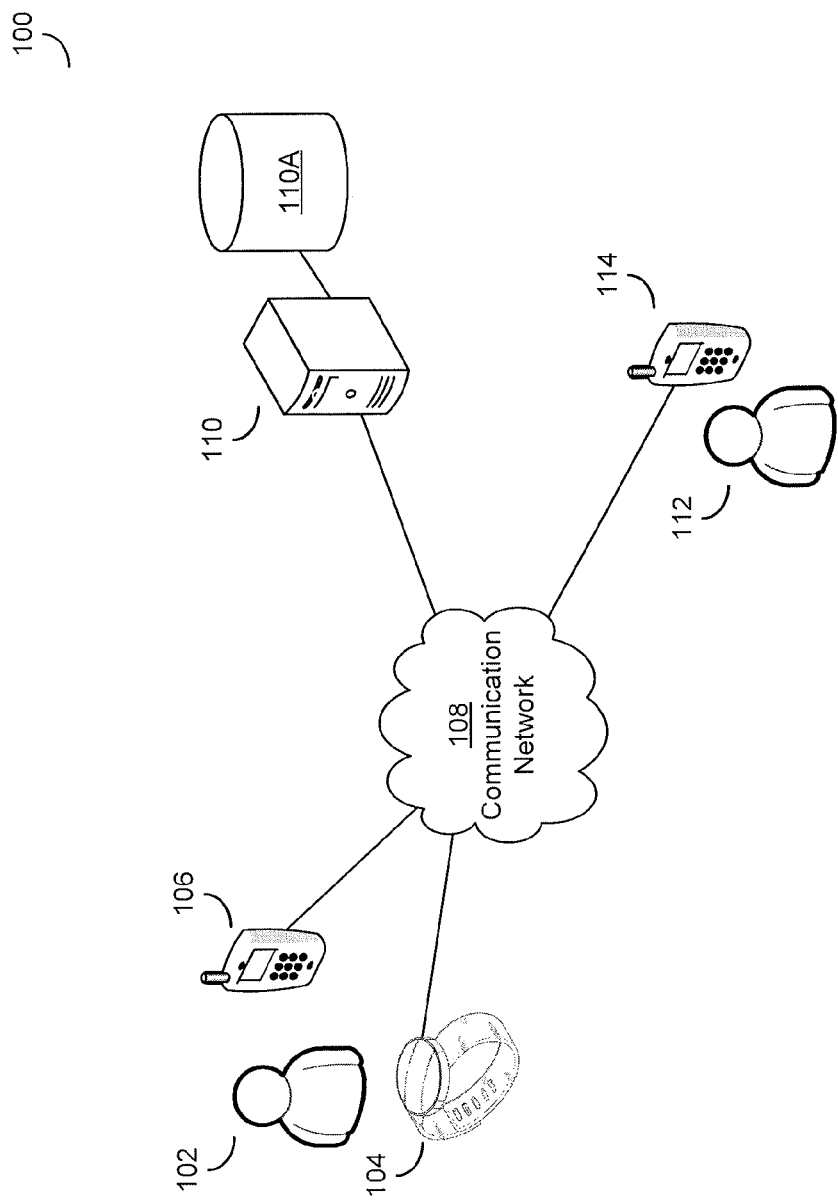
FIG. 1 is a diagram of illustrative components of a computer system with which some embodiments may operate.

Described herein are embodiments of a device to predict the occurrence of seizures for a person based on biological information for the person. Such a device may, for example, be able to predict seizures potentially hours or a day in advance of a seizure, such as by generating a prediction that is applicable for a 24-hour period or another period of time (e.g., more than two hours and less than 8, 10, 12, or 24 hours) following the prediction. The device may monitor various biological characteristics to form the prediction, such as by monitoring an electrodermal activity (EDA) on a surface of the person's skin and/or a body temperature of the person. In examples of such devices described below, the device may identify sleep periods and wake periods for the person, such as by identifying periods of lower and higher movement from analyzing accelerometer signals. In some embodiments, the device may then compare biological information between a wake period and a following sleep period and generate a prediction of an occurrence of a seizure based on the comparison. For example, the device may analyze EDA and/or temperature for a wake period and a succeeding sleep period, calculate ratios for EDA and/or temperature between the wake period and the sleep period, and generate a seizure prediction for the person based on the ratios. In some such embodiments that analyze sleep and wake periods, the seizure prediction that is generated by the device may be a prediction of whether the person will or will not have a seizure in the wake period immediately following the wake/sleep period on which the prediction is based.

The inventors have recognized and appreciated that patients would benefit greatly from a reliable way of predicting whether a person will have a seizure in a particular time period. Several techniques have been proposed for seizure detection, which may include informing epilepsy patients or caregivers of a seizure that is currently in progress or is imminent. However, techniques for seizure prediction are not readily available. The inventors have recognized and appreciated that, due to the danger inherent in epilepsy, it would be helpful to patients and caregivers to be able to predict the occurrence of a seizure, such as by determining whether a seizure may occur beyond a few seconds following the prediction, such as minutes, tens of minutes, or hours following the prediction. This may give the epileptic patient or a caregiver the ability to plan for the seizure, such as through the patient avoiding placing themselves in a situation in which a seizure may injure others (e.g., driving a car) or through the caregiver keeping a closer watch on the patient.

The inventors have recognized and appreciated that there are various disadvantageous to existing techniques for seizure prediction. Existing techniques focus on predicting seizures using electroencephalograms (EEGs), or more invasive monitoring of the brain. EEGs require a great deal of data regarding electrical activity within a patient's brain and require the placement of many sensors around the patient's skull. Such a procedure is difficult to perform over a long term. The EEG is not designed to be freely mobile, to be used as patients go about their lives, and many patients may feel uncomfortable wearing an EEG monitor for an extended period of time. Moreover, many EEG techniques are only able to generate a reliable prediction of a seizure that applies to a few seconds or minutes following the prediction. The inventors have therefore recognized and appreciated that it would be advantageous to patients to have a device that is non-intrusive and may be used or worn as the patients move through a normal daily routine, and the advantages of a device that generates a reliable prediction of whether a patient will experience a seizure over the course of tens of minutes, hours, or days following generation of the prediction.

Accordingly, examples are described below of techniques for generating a prediction of seizure occurrence and of devices for use with such techniques. In some embodiments, biological characteristics of a patient may be monitored for a first period of time and a second period of time and data relating to the biological characteristics may be compared. Based on a result of that comparison, a prediction may be generated of whether the patient will experience a seizure during a period of time following the second period. In some illustrative embodiments, the first period of time and the second period of time may be a wake period and a succeeding sleep period, respectively, and the period of time following the second period may be a next wake period. Further, in some illustrative embodiments, the biological characteristics of the patient may be a body temperature and/or an electrodermal activity (EDA) of the patient.

FIG. 1 illustrates an example of a system with which some embodiments may operate. In the computer system 100 of FIG. 1, a patient 102 operates a wearable device 104 and a computing device 106. The wearable device 104 is illustrated in FIG. 1 as a wristlet that is shaped and arranged to be worn on and attached to a wrist of the patient 102. It should be appreciated, however, that embodiments are not limited to operating with a wearable device that is arranged to be worn at any particular location on the body and embodiments may instead operate with a wearable device that may be worn at any suitable location on the body. The wearable device 104 may include one or more sensors to collect information that may be analyzed to generate a prediction of whether the patient 102 will experience a seizure. For example, in some embodiments the wearable device 104 may include one or more sensors to detect a body temperature of the patient 102. As another example, the wearable device 104 may additionally or alternatively include one or more sensors to detect an electrodermal activity (EDA) of the patient 102. Those skilled in the art will understand that EDA is a measurement of electrical characteristics of the skin of the patient 102, and may be alternately termed skin conductance, galvanic skin response (GSR), electrodermal response (EDR), psychogalvanic response (PGR), skin conductance response (SCR), or skin conductance level (SCL). In some embodiments, as discussed further below, the wearable device 104 may also include an accelerometer to generate movement information. The wearable device 104 may include a storage to store data collected by the sensor(s).

In some embodiments, the wearable device 104 may include one or more processors or other control circuits configured or programmed to analyze the data on the biological characteristics, and in some embodiments the movement information, to generate a prediction of whether the patient will experience a seizure. For example, the wearable device 104 may store and execute a seizure prediction facility to generate the prediction. Upon generating the prediction, the wearable device 104 may output the prediction via a user interface of the device 104, such as via a display screen, a light (e.g., a light-emitting diode (LED)), a speaker, a vibration circuit, and/or other form of output. In some embodiments, the wearable device 104 may additionally or alternatively transmit the prediction, together with any other suitable information, to the computing device 106 for output, such as via wired and/or wireless transmission components of the wearable device 104. The prediction may be communicated to the device 106 in any suitable manner, including as a voice message, a text message (e.g., SMS message), an email, or other message. For example, the computing device 106 may be implemented as a mobile device such as a smartphone, and the device 104 may transmit the prediction to the mobile device, such as to an "app" implemented on the smart phone, to present the prediction to the patient 102. The computing device 106 is illustrated in FIG. 1 as a smartphone, but it should be appreciated that in embodiments other forms of computing devices may be used, such as laptop or desktop personal computers, personal digital assistants (PDAs), or other devices. In such embodiments, the wearable device 104 may transmit the data via a communication network 108, discussed below.

In some embodiments, the wearable device 104 may also transmit the data on the biological characteristics, and in some embodiments the movement information and/or a generated prediction, to one or more servers 110. The device 104 may transmit the information to the server(s) 110 over the communication network 108. The server(s) 110 may be implemented as any suitable computing device or array of computing devices, as embodiments are not limited in this respect. For example, the server(s) 110 may be a distributed network of servers, a desktop or laptop personal computer, a mobile device, or other computing device to analyze data. In some embodiments, the server(s) 110 may be implemented as a mobile device operated by the patient 102, and may be the same device as the device 106. In other embodiments, the server(s) 110 may be operated by a medical care provider, such as a doctor's office, or by a provider of a seizure prediction service, and may be located remote from the patient 102.

Server(s) 110 may be configured to store the received information in a data store 110A. Information may be stored in the data store 110A in association with an account for the patient 102 or otherwise in association with information identifying the patient 102 to indicate that the information relates to patient 102. In some embodiments, the server(s) 110 may additionally relay information, including the prediction, to other devices that have been associated (e.g., through prior configuration input) in the data store 110A with the patient 102. For example, the data store 110A may store information indicating that the patient 102 is associated with the device 104, the device 106, and/or the device 114 (e.g., via an association between the patient 102 and the caregiver 112). In response to identifying that association, the server(s) 110 may relay information to one or more of those devices.

In some embodiments, the wearable device 104 may not be configured to analyze data to generate a prediction of whether the patient 102 will experience a seizure. Instead, in some such embodiments, the server(s) 110 may include one or more processors or other control circuits to analyze the data and generate the prediction. For example, the server(s) 110 may store and execute a seizure prediction facility to generate the prediction. In such embodiments, the server(s) 110 may store the prediction in the data store 110A and may transmit the prediction to the wearable device 104 and/or the device 106 for output to the patient 102. In such embodiments, the server(s) 110 may transmit the prediction via the communication network 108.

In some embodiments in which the server 110 is separate from the device 106, instead of or in addition to a server 110 receiving the biological data from the wearable device 104, storing the biological data, executing a seizure prediction facility to analyze the data to generate a prediction, and transmitting the prediction to the wearable device 106 for output, the device 106 may be configured to perform this function, including by storing and executing the seizure prediction facility.

In some embodiments, the wearable device 104 and/or the server(s) 110 may additionally communicate to a caregiver 112 the prediction of whether the patient 102 will experience a seizure. Caregiver 112 may be a person who may care for the patient 102, such as a friend or family member of patient 102 or a medical professional such as a doctor or nurse. In some such embodiments, the device 104 and/or server(s) 110 may transmit the prediction, via the communication network 108, to a device 114 operated by the caregiver 112. The device 114 may be any suitable computing device, as embodiments are not limited in this respect. The prediction may be communicated to the device 114 in any suitable manner, including as a voice message, a text message (e.g., SMS message), an email, or other message. For example, the computing device 114 may be implemented as a mobile device such as a smartphone, and the device 104 may transmit the prediction to the mobile device, such as to an "app" implemented on the smart phone, to present the prediction to the caregiver 112. The computing device 114 is illustrated in FIG. 1 as a smartphone, but it should be appreciated that in embodiments other forms of computing device may be used, such as laptop or desktop personal computers, personal digital assistants (PDAs), or other devices.

The communication network 108 by which the devices of system 110 may communicate may be or include one or more wired and/or wireless networks. In some embodiments, the network 108 may include one or more wireless personal area networks (WPAN), one or more wireless and/or wired local area networks (LANs), and/or one or more wireless and/or wired wide area networks (WANs), and in some embodiments may include the Internet.

Figure 2:
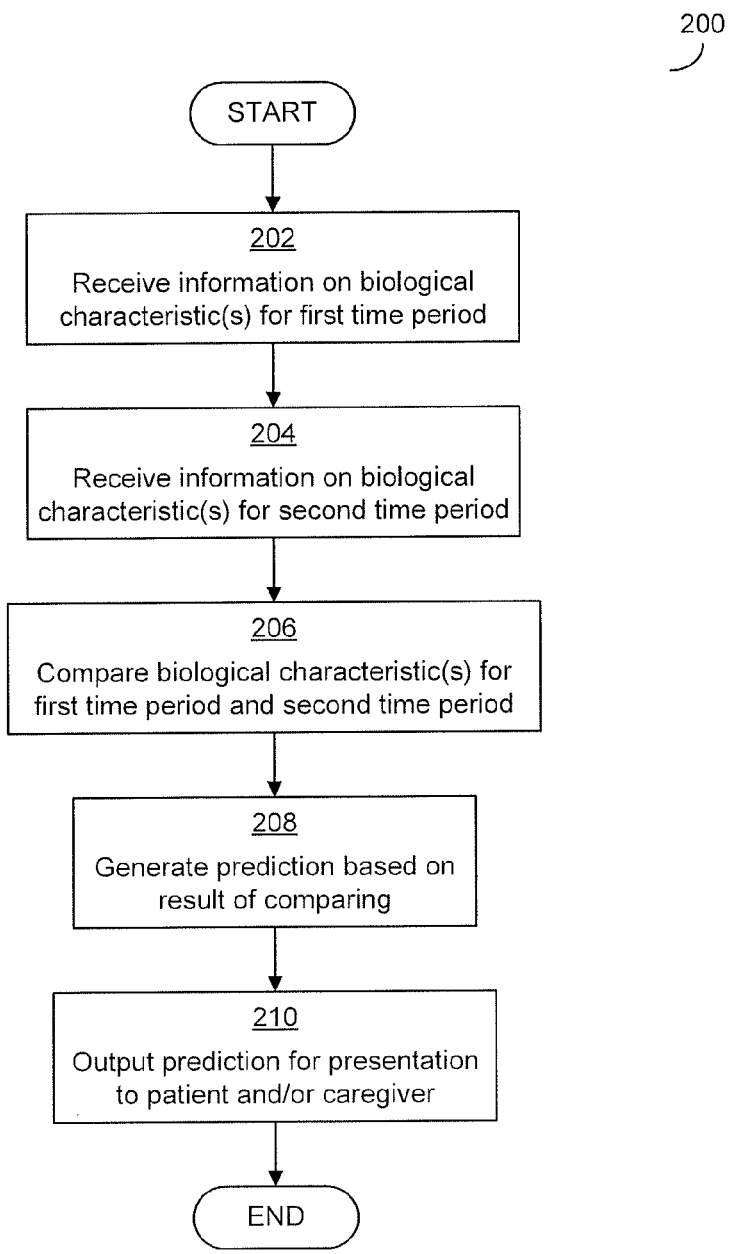
FIG. 2 is a flowchart of an example of a process that some embodiments may implement to predict occurrence of a seizure based on biological characteristics.
Figure 3:
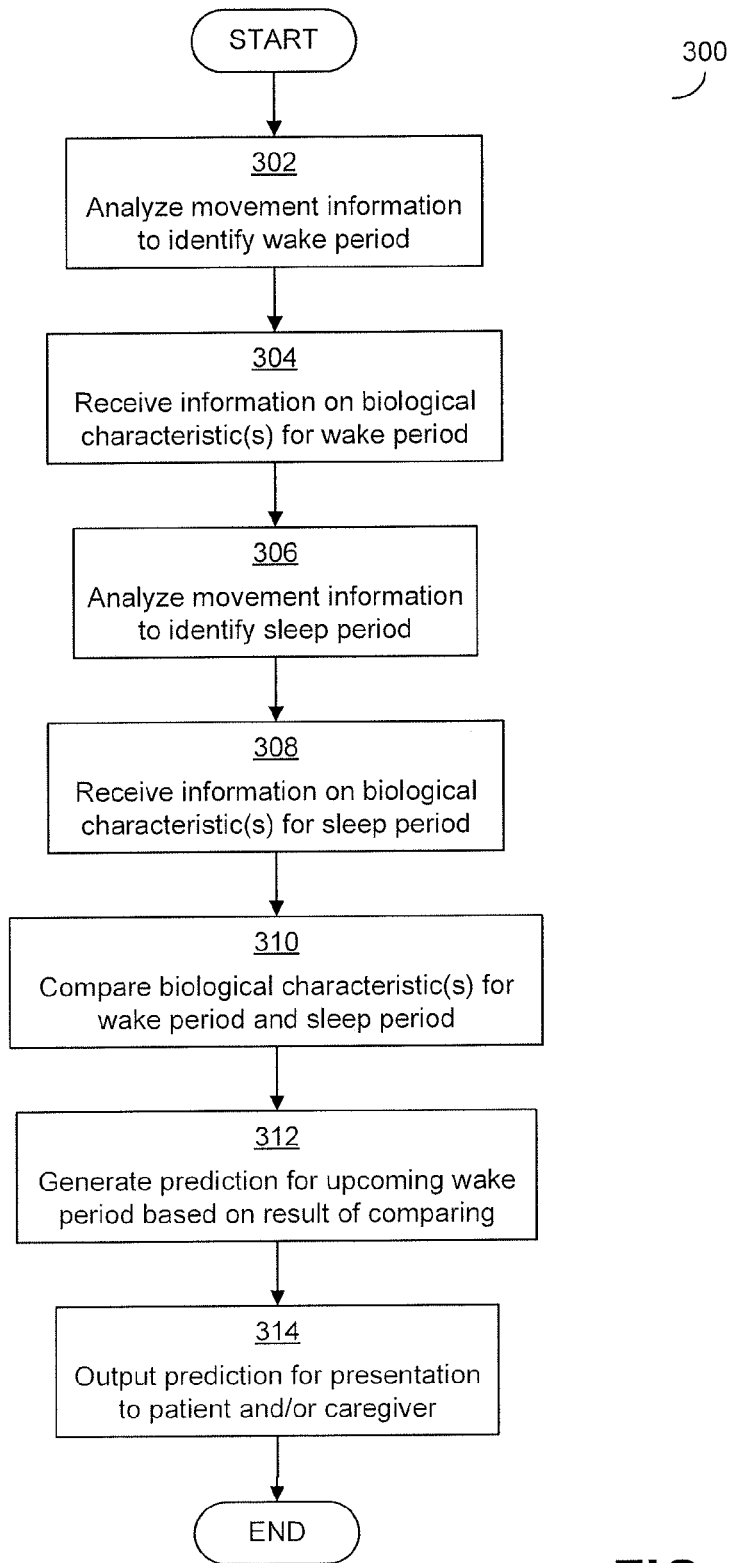
FIG. 3 is a flowchart of an example of a process that some embodiments may implement to predict occurrence of a seizure based on a comparison of biological characteristics in wake and sleep periods.
Figure 4:
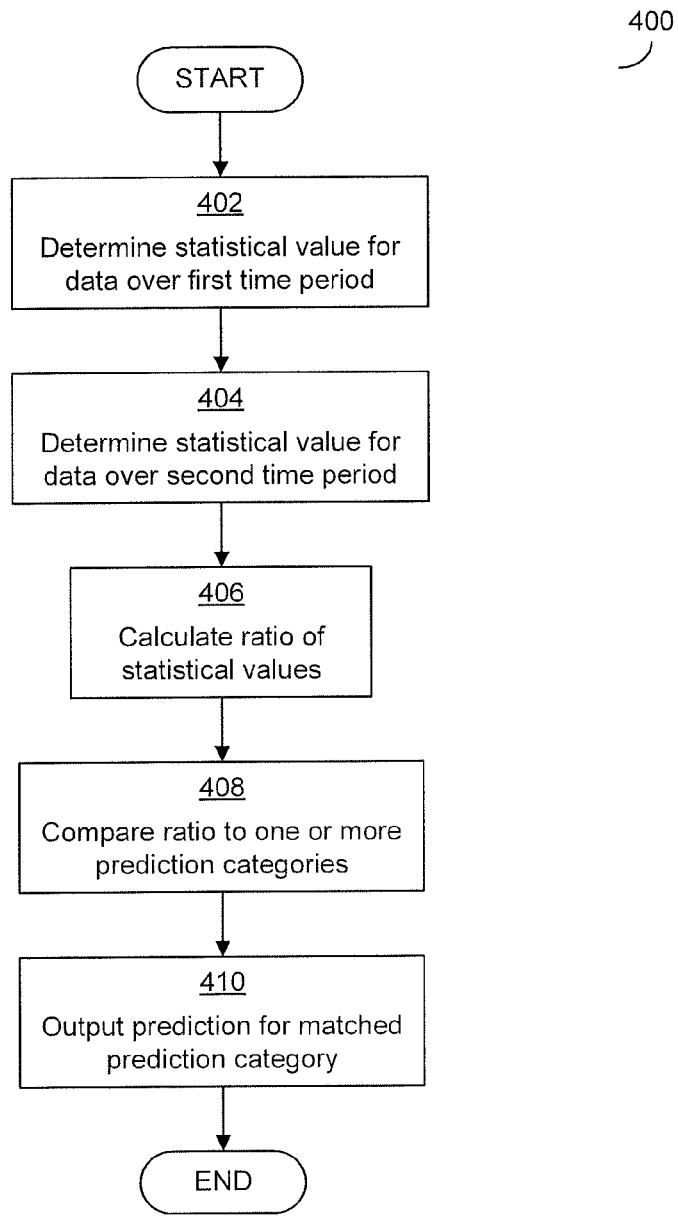
FIG. 4 is flowchart of an example of a process that some embodiments may implement to compare biological characteristics for time periods.

As discussed above, in some embodiments a device (e.g., wearable device 104 and/or server(s) 110) may execute a seizure prediction facility that analyzes biological information for a patient and generates a prediction of whether the patient will experience a seizure. FIGS. 2-4 illustrate examples of processes that may be implemented by such a seizure prediction facility.

Prior to the start of the process 200 of FIG. 2, and/or during the process 200 of FIG. 2, one or more sensors may be monitoring biological characteristics of a patient. For example, a patient may be wearing a wearable device incorporating the sensor(s) and the sensor(s) may be monitoring the biological characteristics and generating data. The data generated by the sensor(s) may include values for biological characteristics that the sensors generated continuously and/or at discrete sampling intervals (e.g., multiple times a second, every minute, every few minutes, several times an hour, or any other suitable interval) and each value may be associated with a time the value was generated. The time may be an absolute time, such as a time of day and/or date, or may be an elapsed time from a reference point such as a start of monitoring, or may be any other suitable time.

The process 200 begins in block 202, in which the seizure prediction facility receives information on one or more biological characteristics for a first time period. The information that is received by data generated by the one or more sensors, such as values for biological characteristics. As discussed above, the data may also include time information. The seizure prediction facility of the example of FIG. 2 is not limited to operating with a particular biological characteristic. In some embodiments, the seizure prediction facility may receive and process information relating to body temperature and/or electrodermal activity, though in other embodiments data for other measurable properties of a human body that may relate to likelihood of seizure occurrence may be analyzed, such as pulse or blood volume pulse.

In block 204, the seizure prediction facility receives information on the one or more biological characteristics for a second time period. The information received in block 204 may be in the same format, and relate to the same biological characteristic(s) as, the information received in block 202.

It should be appreciated that embodiments are not limited to operating in connection with specific lengths of time periods for the first and second time periods of blocks 202 and 204. Example time periods are discussed below in connection with FIG. 3.

In block 206, the seizure prediction facility compares the information on the biological characteristic(s) for the first time period and the second time period. Through the comparison of block 206, the seizure prediction facility determines how the biological characteristics change from the first time period to the second time period. The change in the biological characteristics from the first to the second time period may be a change that is indicative of occurrence of a seizure, and as such by comparing the biological characteristics the seizure prediction facility may be able to predict a potential seizure in a time period following the second time period. The seizure prediction facility is not limited to performing a particular comparison in block 206. Examples of comparisons, and examples of changes in biological characteristics that may be predictive of a seizure, are described below in connection with FIG. 4.

In block 208, the seizure prediction facility generates, based on a result of the comparing, a prediction of whether the patient will experience a seizure during a time period following the second time period. In some embodiments, the facility may output a "yes" prediction, indicating a potential seizure, when the comparison indicates that a change in characteristic(s) matches a change indicative of a seizure, or a "no" prediction otherwise. In other embodiments, the facility may identify a likelihood of a seizure, including a numeric likelihood, a low/medium/high likelihood or other qualitative prediction, or other relative value indicating a chance of a seizure occurring. In some embodiments, to generate the prediction, the seizure prediction facility may be configured with definitions corresponding to various predictions, such as definitions for "yes" and "no" predictions or definitions for "low," "medium," and "high" predictions. The definition may be, for example, one or more conditions to be satisfied, such as a threshold. In such embodiments, the facility may evaluate the result of the comparison of block 206 with respect to the condition(s) for each prediction to determine whether the result of the comparison satisfies a definition for a prediction. When the result satisfies a definition for a prediction, the seizure prediction facility generates that prediction.

In block 210, the seizure prediction facility outputs the prediction for presentation to the patient and/or a caregiver of the patient. The prediction may be output directly via a user interface of the device on which the seizure detection facility is executing, such as in a case that the seizure prediction facility is executing on a wearable device (e.g., wearable device 104 of FIG. 1) and the wearable device includes a user interface. In other embodiments, the prediction may be output in block 210 by storing the prediction to a storage and/or transmitting the prediction via a network to another device. In a case that the output includes transmission via a network, the prediction may be transmitted via the network to a device including a user interface, such as devices that may be operated by the patient and/or the caregiver (e.g., devices 106, 114 of FIG. 1). The seizure prediction facility may output the prediction along with any other suitable information, such as information regarding the biological characteristic(s) that were analyzed and/or a result of the comparing, or a time period over which the prediction is valid.

Once the prediction is output in block 210, the process 200 ends.

The process 200 of FIG. 2 was described as operating with time periods, including by comparing biological characteristics for first and second time periods to generate a prediction for a time period following the second time period. It should be appreciated that embodiments are not limited to operating with particular time periods. In some embodiments, the time periods for which biological information is received and compared may be several hours, such as time periods that extend for between two and twenty-four hours, and the time period for which the prediction is generated may be for several hours, such as between two and twenty-four hours immediately following the second time period.

In some embodiments, the time periods may be fixed by an operator of a seizure prediction facility, such as a developer of the facility or a user such as the patient or a caregiver. In other embodiments, the time periods may be automatically determined from an analysis of data regarding biological characteristics and seizures, as discussed below in connection with FIG. 5. In the case that time periods are automatically determined, time periods may be of varying length, including time periods of several hours, several days, or several weeks.

FIG. 3 illustrates an example of a process that may be used in some embodiments, in which the time periods with which a seizure prediction facility operates relate to a circadian rhythm of a patient and, more specifically, to sleep and wake periods for the patient. As discussed in detail below in connection with FIG. 3, the process may include operating with a first period that is a wake period in which the patient is awake and a second period that is a sleep period immediately following the wake period and in which the patient is asleep. In this embodiment, the seizure prediction facility may generate a prediction of whether the patient will experience a seizure during the next wake period and/or the next wake and sleep periods.

The process 300 of FIG. 3 begins in block 302, in which movement information for a patient is analyzed to identify a wake period for a patient. The movement information may be information generated by an accelerometer, such as an accelerometer integrated into a device that may be worn by the patient and that includes sensors for sensing biological information for the patient (e.g., the device 104 of FIG. 1). In such embodiments, the movement information may be information indicating a movement of a part of the patient's body on which the device is worn, such as movement of a wrist. By analyzing movement information to determine periods of movement and non-movement, and/or comparing movement information to known characterizations of the amount of movement of typical people during sleep and/or wake, the seizure prediction facility may identify a wake period for the patient.

In block 304, the seizure prediction facility receives information on one or more biological characteristics of the patient during the wake period. The biological characteristic(s) may be or include characteristics discussed above in connection with FIG. 2 and the information may include data and be in a format discussed above in connection with FIG. 2.

In block 306, the seizure prediction facility analyzes movement information to identify a sleep period for the patient, which the facility may perform as described above in connection with block 302.

The seizure prediction facility then, in block 308, receives information on the biological characteristic(s) of the patient during the sleep period, which may be the same information on the same characteristic(s) for which information was received for the wake period in block 304.

In blocks 310, 312, and 314, the seizure facility may compare the information on the biological characteristic(s) for the wake and sleep periods, generate a prediction based on the comparison, and output the prediction. As discussed above, in the example of FIG. 3, the prediction that the facility generates may be a prediction of whether the patient will experience a seizure during a wake period, or a wake and sleep period, immediately following the sleep period identified in block 306. The comparison, generation of a prediction, and output of a prediction may be carried out in the manner described above in connection with blocks 206-210 of FIG. 2. Once the prediction is output in block 314, the process 300 ends.

As discussed above in connection with FIG. 2, embodiments are not limited to comparing biological information in a specific manner. FIG. 4 illustrates an example of a comparison that may be implemented in some embodiments, such as the illustrative embodiments of FIGS. 2-3. Prior to the start of the process 400 of FIG. 4, a biological characteristic of a patient may be monitored and data for that characteristic over two periods of time may be received.

The process 400 begins in block 402, in which the seizure prediction facility calculates a statistical value for data relating to a biological characteristic over a first time period. The facility is not limited to calculating a particular statistical value. In some embodiments, the statistical value may be a mean value over the time period, while in other embodiments other statistical values such as median, mode, variance, a distribution of values over the time period, or other value may be calculated. In block 404, the seizure prediction facility performs a similar calculation on values for a second time period to generate a statistical value for a second time period.

As discussed above, the process 400 may be used to compare data for two time periods. In the example of FIG. 4, the comparison is done through calculation of a ratio. Specifically, in block 406, the seizure prediction facility calculates a ratio of the statistical value for the second time period, calculated in block 404, to the statistical value for the first time period, calculated in block 402. Embodiments are not limited to performing a comparison through a ratio, however. In other embodiments, a difference between the two statistical values may be calculated. Other mathematical operations may also be performed to calculate a relationship between the first statistical value and the second statistical value, and may in some cases depend on the form of the statistical values (a single numeric value, a distribution, etc.).

The ratio of the second statistical value to the first statistical value may indicate how a biological characteristic changed from a first time period to a second time period, such as from a wake period to a succeeding sleep period. Such a change may be indicative of a seizure occurring following the second time period, such as in a wake period immediately following the sleep period. The inventor has recognized and appreciated, for example, that certain oscillations in body temperature during a sleep period, when compared to oscillations in body temperature during a preceding wake period, may be indicative of a seizure. More details are provided below in a section on experimental results. The inventor has recognized and appreciated that such oscillations may be quickly identified and analyzed through a comparison of mean values or other statistical values, and that a change in such oscillations may be captured through a ratio in such mean values. Accordingly, in block 406, the ratio is calculated.

For ease of explanation, the operations of blocks 402-406 were described above in connection with a single biological characteristic for each of the first and second periods, and a single comparison in block 406. In embodiments, however, multiple characteristics may be evaluated and, in such cases, multiple statistical values may be calculated and multiple comparisons may be performed. In such embodiments, the statistical values and comparisons may be of a different form between different biological characteristics, rather than all being the same (e.g., all being ratios of means).

The seizure prediction facility then, in block 408, compares the ratio to one or more definitions for one or more prediction categories. The prediction categories may be qualitative categories associated with likelihood of seizure occurrence, such as a binary "yes" or "no" prediction or a prediction with more levels such as "low," "medium," or "high." Each category may be associated with a definition that, when met by a result of the comparison of block 406, indicates that the prediction associated with that category applies to the patient at that time and should be generated/output by the seizure prediction facility. Embodiments are not limited to operating with particular definitions. In some embodiments, a definition may include one or more conditions against which the result of the compared is evaluated. The condition(s) may be, for example, one or more thresholds, each of which may be associated with one biological characteristic. Specific examples of thresholds that may be used for body temperature, and predictions corresponding to those thresholds, are described below in the section on experimental results.

In block 410, once the seizure prediction facility has identified, based on the definitions for prediction categories evaluated in block 408, a prediction to generate, the facility outputs the identified prediction for a matched category in block 410. The output of the prediction may be done as discussed above in connection with block 210 of FIG. 2. After the prediction is output, the process 400 ends.

In examples above, particular time periods for data collection and evaluation were discussed, such as wake and sleep periods, and time periods to which a prediction applies, such as a subsequent wake period. In addition, in connection with FIG. 4, particular thresholds for biological characteristic data were discussed. In some embodiments, these time periods and thresholds may be selected by a human administrator of the seizure prediction facility and the facility may be manually configured by the human administrator accordingly. In other embodiments, however, these time periods and thresholds, or other time periods and thresholds, may be determined automatically through an automated analysis of biological characteristic data and seizure occurrence data. The automated analysis may be, for example, a machine learning process, such as the machine learning process described in connection with FIG. 1 of "Convulsive Seizure Detection Using a Wrist-Worn Electrodermal Activity and Accelerometry Biosensor" by Poh et al., published in Volume 53, issue 5, of *Epilepsia* in 2012 ("the Poh article"), which is incorporated herein in its entirety and at least for its discussion of machine learning techniques.

Figure 5:
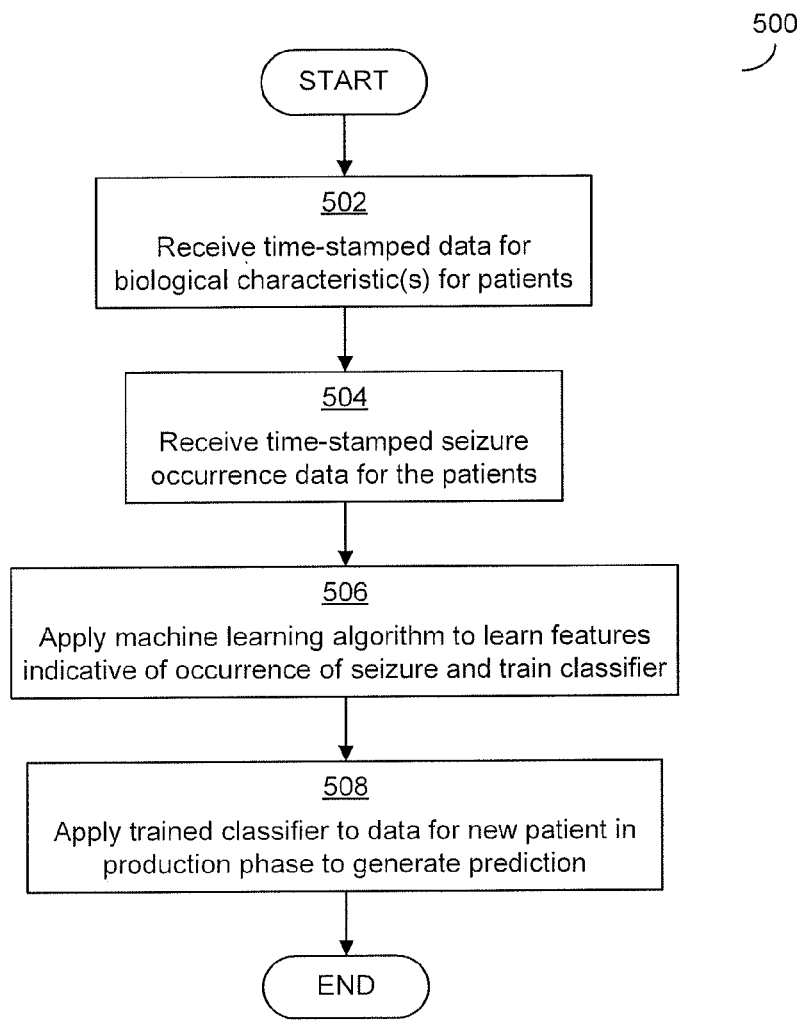
FIG. 5 is flowchart of an example of a process that some embodiments may implement to analyze biological characteristic data and seizure data to identify characteristics and time periods that may be used to predict seizures.

FIG. 5 illustrates a machine learning process that may be implemented in some embodiments to identify time periods, thresholds, or other ways of dividing data regarding biological characteristics for analysis and generation of a prediction of whether a patient will experience a seizure. The process 500 begins in block 502, in which a learning facility receives time-stamped data for one or more biological characteristics over time for each of one or more patients. In some embodiments, the learning facility may also receive for each patient data describing the patient, such as demographic data like the patient's gender and/or patient's age. In addition, in block 504, the learning facility receives seizure occurrence data for each patient that indicates whether that patient has experienced a seizure, and may include time-stamped information about one or more seizures when a patient has had a seizure. In block 506, the learning facility applies a machine learning algorithm to the biological characteristic data and the seizure occurrence data to identify features in the biological characteristic data that may be indicative of a later occurrence of a seizure. The machine learning algorithm that is applied may be the same as or similar to the machine learning algorithm described in the Poh article referenced above. Types of machine learning techniques may be implemented, including machine learning algorithms that employ linear regression, random forest, and robust linear regression. To analyze the biological characteristic data, sliding windows of different lengths may be used to segment the data, such as sliding windows of 10 seconds, 1 minute, 1 hour, 6 hours, 12 hours, and 24 hours. In addition, biological characteristic data for patients may be segmented based on whether patients experienced a seizure or experienced a seizure within a particular time. Through this learning process, a Support Vector Machine (SVM) may be trained with information on biological characteristics that may be indicative of occurrence of a seizure, as well as time periods over which to analyze the characteristics, time periods over which a prediction will be applicable, and definitions for the predictions (e.g., thresholds) that, when met, signal that the prediction should be generated and output. In some embodiments, a learning process may compare predictions for seizures with information relating to actual seizures experienced by the patient, and a result of the comparing may be used to inform training of the learning process and/or select a suitable machine learning technique. In such embodiments, predictions and actual data for seizures may be used to train the learning process.

In block 508, once the support vector machine is trained by the learning facility, the support vector machine itself or data identified by the support vector machine (e.g., time periods, thresholds) may be used in analyzing patient data to generate predictions for patients, such as using processes described above. The process 500 then ends.

Figure 7:
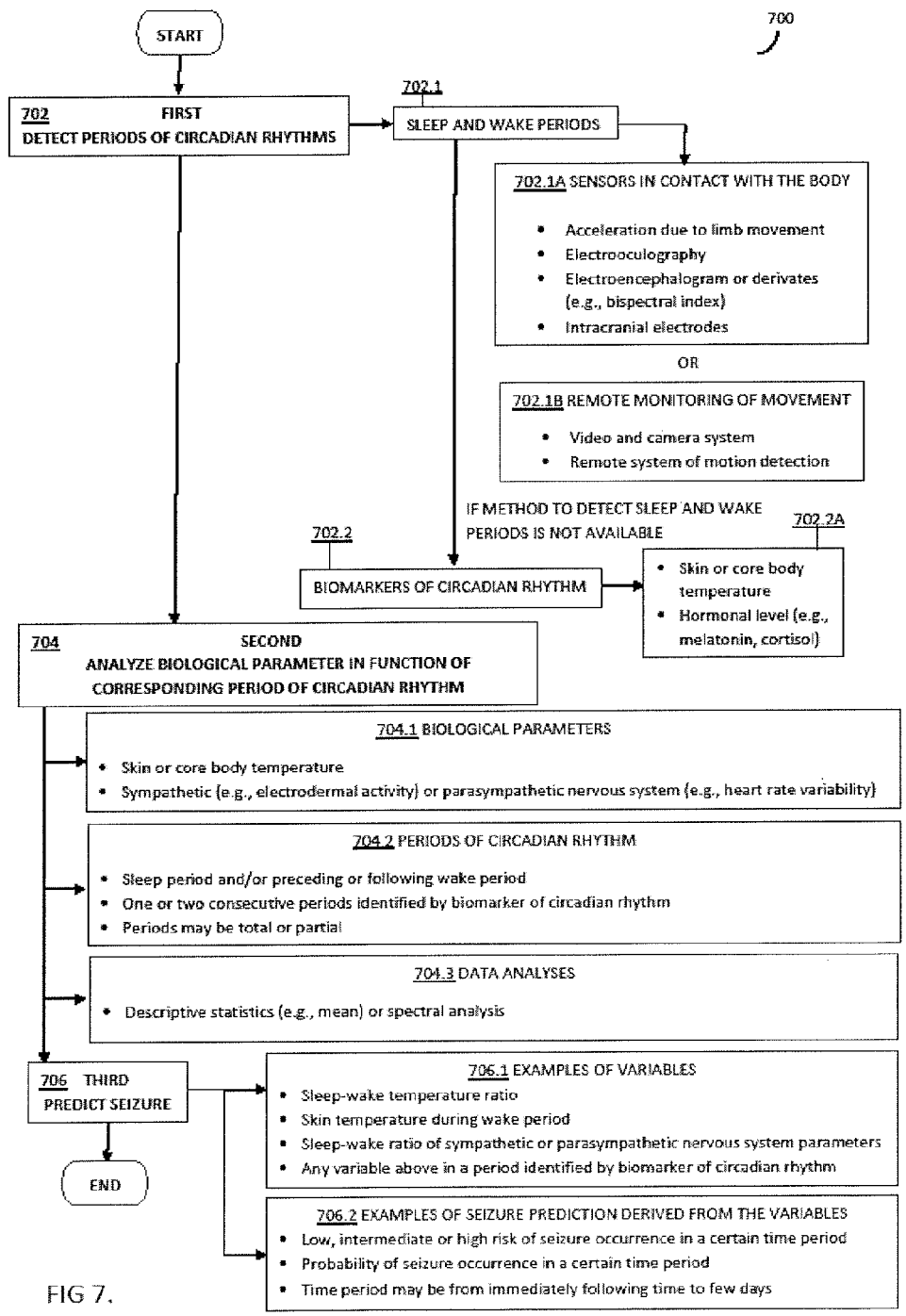
FIG. 7 is a flowchart of an example of a process that some embodiments may implement detailing phases of the process with alternatives in terms of apparatus, data acquisition and analyses, and seizure prediction.

FIG. 7 describes an example of process that may be used in some embodiments to predict seizure, including various phases.

The first phase of the process begins in block 702, in which periods of circadian rhythm of a patient are detected. As shown in block 702.1, periods of circadian rhythm may be sleep and wake periods, for example. Sleep and wake periods may be detected, among other methods, through embodiments with sensors in contact with the body (as shown in block 702.1A) and/or embodiments that perform remote monitoring of movement (as shown in block 702.1B).

Any embodiment with sensors in contact with the body (block 702.1A) that identifies the sleep and wake periods can be used in the system. In a progressive increase of complexity or invasiveness, possible examples of embodiments may be an accelerometer in a wristband device, electrooculography, or methods that detect brain electric activity such as EEG or intracranial electrodes (block 702.1A). Additionally or alternatively, in some embodiments remote monitoring of movement of the patient may be performed (block 702.1B). In embodiments that use remote monitoring, a camera and video system may be included, or any suitable equipment for motion detection (block 702.1B).

There may be situations in which the sleep-wake cycle cannot be identified reliably or may be difficult to identify, for example when the acceleration detected by a wristband device does not include precisely delimited regions of substantial motionlessness and substantial movement that can be identified as sleep and wake periods. In such cases, a sleep-wake cycle can be determined using biomarkers of circadian rhythm (block 702.2). For example, a pattern displayed by the skin temperature monitoring may serve as a biomarker of circadian rhythm (block 702.2A). Skin temperature usually decreases minutes before sleep and increases since the beginning of sleep. In this manner, these parameters serve to estimate circadian periods. Core body temperature may be similarly used (block 702.2A). Core body temperature decreases during sleep. Levels of hormones such as melatonin and cortisol in different body fluids can be used to identify different periods of circadian rhythm (block 702.2A). Other markers for biological characteristics that vary between periods of sleep and periods of waking may be similarly used.

In some embodiments, information on periods of circadian rhythm may be stored in association with time, such as time each characteristic was detected during sleep periods and wake periods, which may facilitate data analysis. Though, analysis can be performed without time and, as such, embodiments are not limited to storing time information.

The second phase of the system (block 704) comprehends the analysis of biological parameters in function of corresponding periods of the circadian rhythm detected in the first phase.

In the second phase (as illustrated in block 704.1), a monitoring device, such as a wristband device that attaches to a patient wrist, senses autonomic functions of the patient such as skin temperature, electrodermal activity, or heart rate variability. In addition (as illustrated in block 704.2), the monitoring device (or another device to which the monitoring device sends data) stores and processes information regarding periods of circadian rhythm. One or more time periods may be analyzed. These time periods may be, for example, sleep period and/or preceding or following wake period, or one or two consecutive periods identified by biomarker of circadian rhythm. As another example, the analysis may be of more than two periods, such as more than a sleep period and a wake period, to identify a trend or tendency over a period of time (e.g., days). The time period of analysis of a biological parameter may be part or the totality of a certain period of circadian rhythm. Data analysis (illustrated in block 704.3) may be performed by a programmed processor (in the monitoring device or the other device that receives the data from the monitoring device), and may include descriptive statistics or spectral analysis of data obtained in blocks 704.1 and 704.2.

The third phase, shown in block 706, includes producing a seizure prediction. An apparatus may display, among other results, a variable (e.g., skin temperature during wake), a ratio between two variables (e.g., sleep-wake temperature ratio, here defined as the mean skin temperature during sleep divided by the mean skin temperature during the preceding wake period), and/or a seizure prediction derived from the variables. The prediction that is produced may be a qualitative prediction, such as high, intermediate or low risk of seizure occurrence, or a quantitative prediction, such as a probability of seizure occurrence. The prediction may be applicable to a certain time period, which may vary from a short time immediately following the prediction (e.g., the next few hours, or the next day) to a few days (e.g., two, three, or up to seven days).

Following the third phase, the process 700 ends.

One skilled in the art can perform the phases of the system described in FIG. 7 as an example of seizure prediction system. It should be appreciated that the process of FIG. 7 is only an example and that other processes may be implemented. The illustrative phases of FIG. 7 may be developed and executed in other manners.

Described below is a particular protocol that may be used to predict seizure using a wristband device that senses acceleration, electrodermal activity, and temperature. This protocol is merely illustrative, as other protocols may be used.

Example of a Protocol to Predict Seizure

1) Detect periods:
 1.1 monitor acceleration, temperature, and EDA with wristband device during wake and the following night sleep period,
 1.2 take off the wristband when the patient awakes and save the monitoring data onto a computer,
 1.3 open the file with any appropriate software,
 1.4 analyze acceleration line to identify sleep and the previous wake periods,
 1.5 determine the beginning and end time of the sleep and preceding wake periods, and
 1.6 complementary, perform qualitative analysis of temperature and electrodermal activity.

2) Analyze parameters:
 2.1 export data containing (a) the beginning and end time of the sleep and preceding wake periods, and (b) temperature and EDA values acquired at a given frequency (e.g., 4.8 or 32 Hz) encompassing at least the sleep and preceding wake period, and
 2.2 obtain mean wrist temperature during sleep (Ts), mean wrist temperature during wake (Tw), Ts/Tw, mean EDA during sleep (EDAs), mean EDA during wake (EDAw), and EDAs/EDAw.

3) Predict seizure:
 3.1 compare variables obtained with variables from clinical study or databank,
 3.2 Determine risk of seizure occurrence, for example:
  Ts/Tw<1.05—high risk of seizure occurrence,
  Ts/Tw=1.05-1.10—intermediate risk of seizure occurrence,
  Ts/Tw>1.10—low risk of seizure occurrence
  (Risk of seizure occurrence in a period of 3-4 days)

Figure 8:
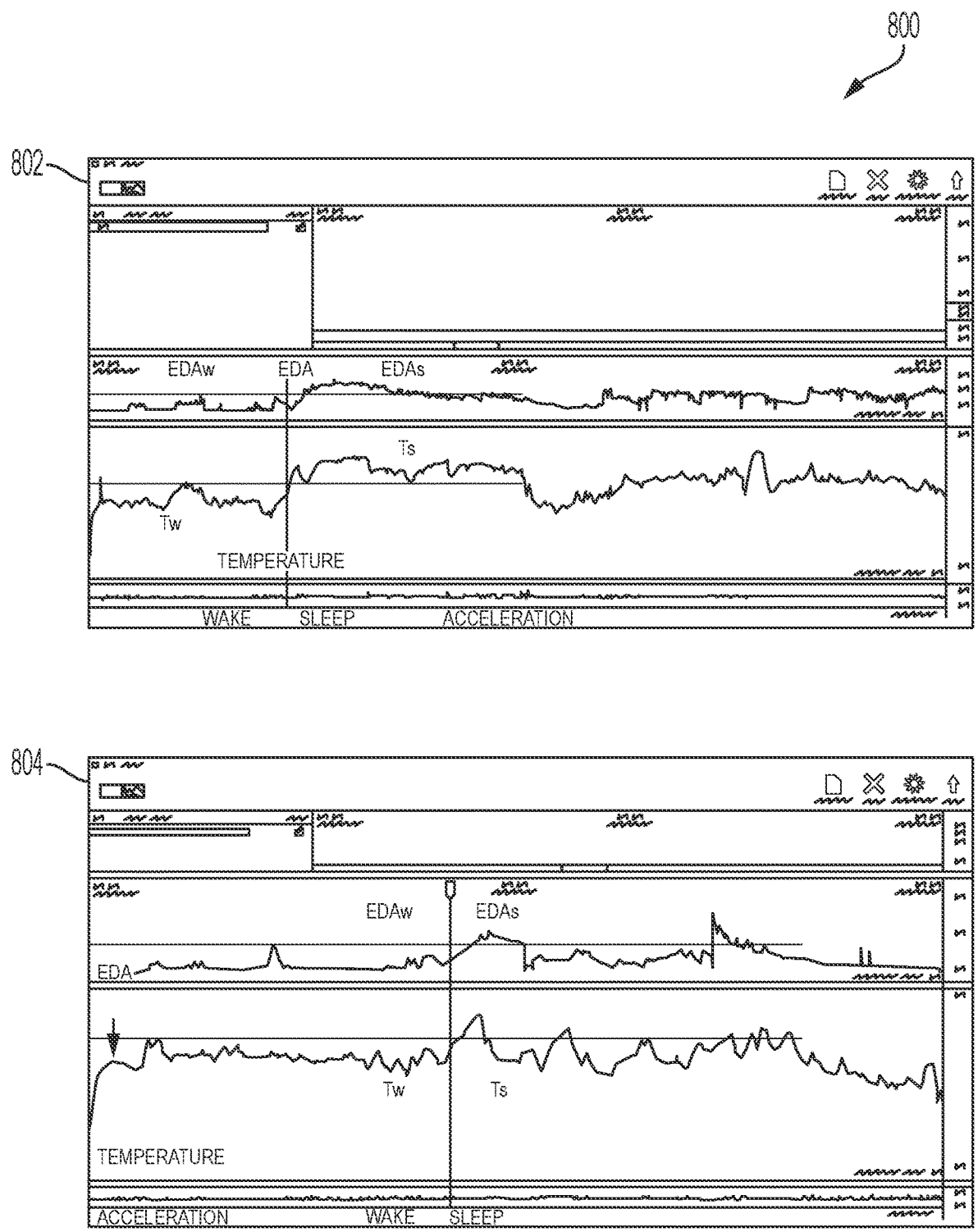
FIG. 8 includes images obtained using software monitoring biological parameters in accordance with techniques described herein.

FIG. 8 includes images generated from data collected by software used to monitor acceleration, temperature, and EDA. These images were analyzed according to the illustrative protocol described above. Note that a qualitative analysis shows (in image 802) in this example that both temperature and EDA are predominantly higher during sleep than during wake. The same pattern is not displayed in image 804. Image 802 is derived from data for a patient that did not display seizure in the days following the monitoring, and image 804 is derived from data for a patient that displayed seizures in the days following the monitoring.

The following section discusses an analysis of 24 cases using the protocol described above.

Experimental Results

Described above are various examples of processes and devices that may be used in embodiments for seizure prediction. An example of patients with which these devices and techniques may be used is described below to provide a detailed example of how techniques described herein may be used to generate predictions of seizures for patients.

In the study, data from epileptic children was monitored by video-EEG and a wristband device that continuously measured the temperature of a patient's wrist, EDA of a patient's wrist, and acceleration of the wrist to detect forearm movement and, as described below, infer sleep and wake periods. Mean temperature in ° C. and EDA in μS during wake and sleep in the first wake-sleep cycle (Tw, Ts, EDAs and EDAw) and the ratios Ts/Tw and EDAs/EDAw for each case were correlated with seizure occurrence in the following days.

More specifically, video-EEG was performed during 3.17±2.28 days in 24 children with mean age equal 8.62±6.45 years. Seventeen children displayed seizures after the first wake-sleep cycle. The results for children with and without seizures were respectively Ts=33.93±1.49 and 34.97±1.76, Tw=33.02±1.38 and 31.75±1.26, Ts/Tw=1.03±0.04 and 1.10±0.04, EDAs=1.86±1.38 and 2.02±2.36, EDAw=1.66±2.35 and 0.63±0.45, and EDAs/EDAw=1.95±1.56 and 4.55±3.69. The most significant differences were observed for Ts/Tw (p=0.002), Tw (p=0.045), and EDAs/EDAw (p=0.061).

From this experiment, we concluded that the ratio of mean temperature (potentially together with EDA, or EDA alone) during sleep and the preceding wake period and the mean temperature during wake may predict seizures in the following days in epileptic children. These findings have potential implications for the management of seizures and sudden unexpected death in epilepsy.

The inventors recognized and appreciated that seizures display reciprocal influences with two processes that are apparently unconnected: circadian rhythms and neurogenesis. However, circadian rhythms are controlled by the suprachiasmatic nucleus in the hypothalamus, a structure also involved in autonomic functions and adult neurogenesis. Moreover, recent reports revealed that adult neurogenesis displays cyclic features. The inventors therefore recognized and appreciated that circadian rhythms may be related to endogenous mechanisms of brain repair in epilepsy.

The study was conducted to investigate a potential relationship between a circadian pattern of autonomic functions and seizure occurrence. Through the study, the inventors determined that the temperature and electrodermal activity (EDA) display a pattern in the wake-sleep cycle that may be predictive of seizures in the following days in epileptic children. This discovery enabled the inventors to then develop a prediction method and a wristband device to increase the accuracy of seizure prediction and prevent sudden death in epilepsy (SUDEP), which is related to the number of seizures and autonomic dysfunction. Examples of such a prediction method and device are discussed above.

The study was carried out at the Department of Neurology of Boston Children's Hospital. Epileptic children hospitalized for video-electroencephalogram (EEG) monitoring had a concomitant monitoring of wrist temperature and EDA using a wristband device since the first day of hospitalization. Time synchronization among the wristband device, hospital server and video-EEG equipment was performed before the beginning of the monitoring of the wrist temperature and EDA using the Q live software. Wristband monitoring was performed at 8 Hz, and data from the wristband device was transferred daily onto a computer until the end of the video-EEG monitoring. Clinical information was obtained accessing the patient electronic chart in a hospital server. Seizure analysis was reviewed using the video-EEG monitoring report.

Temperature, EDA and acceleration were analyzed as follows. First, a qualitative analysis was carried out using the Q software. A visual analysis of the acceleration line allowed the identification of the periods with and without forearm movement, which were regarded as periods of wake and sleep, respectively. The first sleep period was defined as being the first post-6 p.m. period longer than three hours without sustained acceleration; sustained acceleration was defined as acceleration longer than 15 minutes. The end of the preceding wake period was defined as being the second before the beginning of the first period of sleep. The beginning of the preceding wake period was the time in the period with acceleration in which the temperature monitoring was equilibrated with the wrist temperature.

A quantitative analysis was then performed after visual identification of the first wake-sleep period. The data of the wristband monitoring including time identification were exported from the Q software as a CSV file. Mean temperature and mean EDA were calculated for the first wake and sleep periods; these values are referred to as Tw, Ts, EDAw and EDAs in this section on experimental results. Ratios and differences for mean temperature and mean EDA during sleep and wake for each patient were then calculated, which are referred to as Ts/Tw, Ts-Tw, EDAs/EDAw and EDAs-EDAw in this section on experimental results. Two patient groups were defined for the study: patients with or without seizures after the first wake-sleep cycle, which are referred to as the S group and NS group, respectively, in this section. For further analysis, the S group were divided into two sub-groups, formed by patients with or without seizures during the first wake-sleep cycle. Statistical inference was performed by Mann-Whitney-Wilcoxon test using the IBM-SPSS software.

Results were derived from data for 24 patients, from an original patient population of 48 patients. Patients' data was excluded from the analysis based on receiving diagnoses other than epilepsy, poor recording of acceleration, or poor recording of both temperature and EDA. Ten patients were female and 14 were male. Age ranged from 0 to 23 years, with mean age equal 8.62±6.45 years. Time of video-EEG monitoring ranged from 1 to 10 days, with mean time equal 3.17±2.28 days. Time of the first wake and sleep periods ranged respectively from 2 h 39 min to 12 h 05 min and 3 h 05 min to 11 h 46 min, with mean time respectively equal 363±157 min and 479±130 min.

Characteristics of the Groups with and without Seizures after the First Wake-Sleep Cycle Fourteen patients displayed electroclinical seizures after the first wake-sleep cycle, and were included in the S group. Six of these patients were female and eight were male, and age ranged from 0 to 18 years (mean age 7.65±6.02 years). Morbidities associated with the epilepsy were identified in nine patients (53%). Eleven of the patients in the S group (65%) also displayed electroclinical seizures in the first wake-sleep cycle.

Seven patients displayed no electroclinical seizures after the first wake-sleep cycle, and were included in the NS group. In this group, no patients displayed electroclinical seizures during the first sleep-wake cycle. Four patients in this group were female and three were male, with age ranging from three to 23 years (mean age 11±7.33). Morbidities associated with the epilepsy were present in three patients.

Qualitative Analysis
Identification of the First Wake-Sleep Cycle

The first wake-sleep cycle were normally identified in a graph. First, parts of an acceleration curve with or without vertical lines, which represent movement through the tree axis, revealed wake and sleep periods. The second aspect identified was an ascending beginning of a temperature curve for approximately 10-20 minutes until the temperature sensor reached an equilibrium with the wrist temperature. The time after this equilibrium displaying acceleration was interpreted as the beginning of the first wake period.

Temperature

Patterns in the qualitative analysis of the temperature differed between the S and NS groups. Both groups displayed a decrease in the temperature a few minutes in the end of the wake period, but this decrease was normally more remarkable in the NS group. In the NS group, the temperature tended to display a fast increase in the beginning of the sleep, an oscillation in cycles shorter than one hour in general, a level higher than the temperature peaks during the previous wake period, and a peak in the end of the sleep period. In the S group, the temperature tended to increase in the beginning of the sleep, but with oscillations in cycles longer than one hour in general, and with decreases to levels below the temperature peaks during the preceding wake period.

EDA

The differentiation between the S and NS group using the visual analysis of the EDA curve was less clear, but in general the EDA increased in the beginning of the sleep parallel with the temperature increase, and this pattern was more clear in the NS group.

Quantitative Analysis

Temperature

Tw values were lower in the NS ($p=0.045$), and Ts/Tw and Ts-Tw were higher in the NS ($p=0.02$ in both cases). Additionally, Ts/Tw ratios were higher in the NS group in comparison to the sub-group in the S group that did not displayed seizure in the first wake-sleep cycle ($p=0.02$).

EDA

Only in one case the EDA was not recorded properly, showing a flat line corresponding to value zero during most of the wake period, although the wristband device has registered the temperature adequately. The EDAs/EDAw ratios were higher in the NS group (marginally significant, $p=0.061$). However, the ratios of EDAs/EDAw were not significant in a comparison between the NS group and the sub-group of the S group that did not display seizure during the first wake-sleep cycle ($p=0.123$).

Likelihood of Seizure Occurrence

The ratio Ts/Tw displayed a distribution that delimitated groups with low, intermediate and high probability of seizure occurrence in the following days after a wake-sleep cycle. Accordingly, Ts/Tw higher than 1.10 occurred in 57% of patients in the NS group and in no patients in the S group. Ts/Tw between 1.05 and 1.10 occurred in 43% of the patients in the NS group and in 24% of patients in the S group. Ts/Tw lower than 1.05 occurred in no patients in the NS group and in 76% of the patients in the S group.

The inventors have recognized and appreciated that a major harm for epileptic patients is the lack of an effective method to predict seizures. Seizure prediction could guide patient's daily activities, reduce the risk of injuries, improve the treatment of epilepsy, and possibly prevent SUDEP. Epilepsy affects approximately 0.5-0.8% of the world population, and major efforts have previously been applied to develop a seizure prediction method. The focus of these prior searches has been on the analysis of brain electrical activity assessed by EEG or invasive methods. Although progress has been achieved with this approach, a practical and reliable method to predict seizures has not been developed yet.

Apart from such quantitative analyses, some autonomic and emotional symptoms and observations that seizure may occur in a cyclic manner have served as an alternative method for predicting seizures. Some patients display a relatively high ability to predict their seizures by observing mood changes and premonitory symptoms. Moreover, epilepsy and circadian rhythms display reciprocal influences, and the wrist temperature has been shown to be a marker of circadian rhythm. Studies in adults show that, contrary to core body temperature, the wrist temperature increases during sleep. This circadian oscillation suffers minimal influence of environmental factors and displays values below the values of axillary temperature. The inventors recognized and appreciated that, taken together, these findings suggested that analysis of autonomic functions and circadian rhythms might reveal a pattern associated with the occurrence of seizures.

The study described above led the inventors to discover that the higher the potential of the body to maintain a low skin temperature during wake and to increase this temperature during sleep, the lower the probability of seizure occurrence in the following days. The values of wrist temperature during the wake-sleep cycle in the NS group are similar to the values of wrist temperature during the wake-sleep cycle in normal adults.

The inventors further recognized that these findings may explain the reasons for which fever and sleep alterations facilitate seizure occurrence. Fever may diminish the proportion of increase of the skin temperature during sleep. Sleep alterations could hamper processes that might enhance seizure control. It is interesting to note that when patients in the study were detected to have slept in the early afternoon, there was an increase in skin temperature in the NS group. This finding may represent a useful recommendation for epileptic patients.

In practice, the patterns appearing after arousal in the morning may guide the treatment or self-care of epilepsy patients during the following day. Increase of wrist temperature during sleep lower than 5%, between 5-10%, or higher than 10% respectively indicate high, moderate, and low risk to display seizure. Because the intensity of temperature increase may be due to a lower temperature during wake in the NS group and not to a higher temperature during sleep in the same group, future studies may pursue an optimization of the treatment with current or novel drugs that lead to a decrease in the skin temperature during the day.

The results of the patterns of the EDA and temperature ratios are similar, which suggests that alterations in circadian oscillations of autonomic functions as a whole contribute to seizure onset. In the NS group in the study, an ascending curve of EDA in the beginning of the sleep period usually paralleled a similar curve for temperature. The ratio EDAs/EDAw is less significant than the counterpart ratio for temperature, however, it is possible that the analysis of cycles other than the wake-sleep cycle and the analysis of other autonomic functions improve the sensibility and specificity of the method described in this study.

Indeed, seizure prediction by the percentage of skin temperature increase during sleep may be improved by the analysis of autonomic function cycles with frequencies higher than the sleep-wake cycle. Accordingly, cycles of temperature oscillation during sleep in the NS group of the study tended to be shorter than in the S group, usually lasting less than one hour on average. Changes in EDA during the different phases of sleep may improve the method described in this study. In this regard, EDA tended to increase in the beginning of the sleep in the NS group, and it has been shown that the number of EDA storms during the slow wave sleep in the first quarter of sleep correlates with a better subjective quality of sleep.

Cycles with frequencies lower than the sleep-wake cycle seem to be a biomarker for seizure prediction. This result comes from the comparison between the NS group with the sub-group of the S group that did not display seizure during the first wake-sleep cycle. In this case, the ratio EDAs/EDAw is not significant to predict seizure, indicating that the pattern displayed by this ratio may change when a period of days or weeks is analyzed. In other words, for patients in the S group, the capacity to predict seizures analyzing the EDA may be higher or lower according to a cycle that may last days or weeks.

Broadly, Ts/Tw may underpin the improvement of the seizure prediction method by the analysis of cycles with different frequencies of autonomic functions. Because the general pattern seems to indicate that the autonomic functions are integrated in endogenous mechanisms of seizure control, one might speculate that the parasympathetic nervous system (assessed, for example, by heart rate variability), EDA and temperature may be included in a formula to provide the probability of seizure occurrence with a certain time of antecedence. This probability may be tailored to each patient with the results obtained with the monitoring of autonomic parameters for a long period, and may depend on factors such as seizure type, diagnosis of epileptic syndrome, presence of brain lesions and co-morbidities.

Further prospective studies of large series may confirm the results, but the data available provide information on the probability of seizure occurrence in terms of low, intermediate, or high risk. Importantly, the detection of high risk of seizure occurrence should be accompanied by the alert for risk of SUDEP. Currently there is no method to estimate SUDEP risk, but our results show that there is a relationship between autonomic failure and seizure occurrence, and SUDEP may be the extreme of a spectrum of autonomic failure in epilepsy.

The mechanisms that explain the results remains to be determined, but the hypothesis of this study was elaborated with basis on the description of a potential neurogenic system in the human brain. The neurogenic system is a system through which neurogenesis occurs in a coordinated manner in a broad brain area. A crucial structure in this system is the hypothalamus, which plays a major role in the control of cyclic biological rhythms (with different frequencies) and autonomic functions. Accordingly, cyclic biological rhythms and autonomic function may coordinate neurogenesis, and seizures may serve to compensate the lack of effective neurogenesis. In its turn, neurogenesis may be an endogenous mechanism of brain repair that rises from structures such as the hypothalamus and potentially reaches brain zones with insufficient number of neurons such as epileptogenic tissues. In epilepsy, perhaps the neurogenic system does not yield sufficient neurons of yields novel neurons that migrate wrongly following previous heterotopic neural circuitry. If this mechanism exists, than the cyclic pattern of autonomic function reflects the functioning of an endogenous mechanism of plasticity orchestrated in the brain as a whole, and may serve to monitor other brain conditions (e.g. autism, head injury, Alzheimer's disease and stroke).

Computer-Implemented Embodiments

Techniques operating according to the principles described herein may be implemented in any suitable manner. Included in the discussion above are a series of flow charts showing the steps and acts of various processes that predict the occurrence of a seizure based on analysis of biological characteristics over time periods. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application.

Some exemplary functional facilities have been described herein for carrying out one or more tasks. It should be appreciated, though, that the functional facilities and division of tasks described is merely illustrative of the type of functional facilities that may implement the exemplary techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. Such a computer-readable medium may be implemented in any suitable manner, including as computer-readable storage media 612 of FIG. 6 described below (i.e., as a portion of a computing device 600) or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

In some, but not all, implementations in which the techniques may be embodied as computer-executable instructions, these instructions may be executed on one or more suitable computing device(s) operating in any suitable computer system, including the exemplary computer system of FIG. 1, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing device (co-located or geographically distributed) dedicated to executing the techniques described herein, one or more Field-Programmable Gate Arrays (FPGAs) for carrying out the techniques described herein, or any other suitable system.

Figure 6:
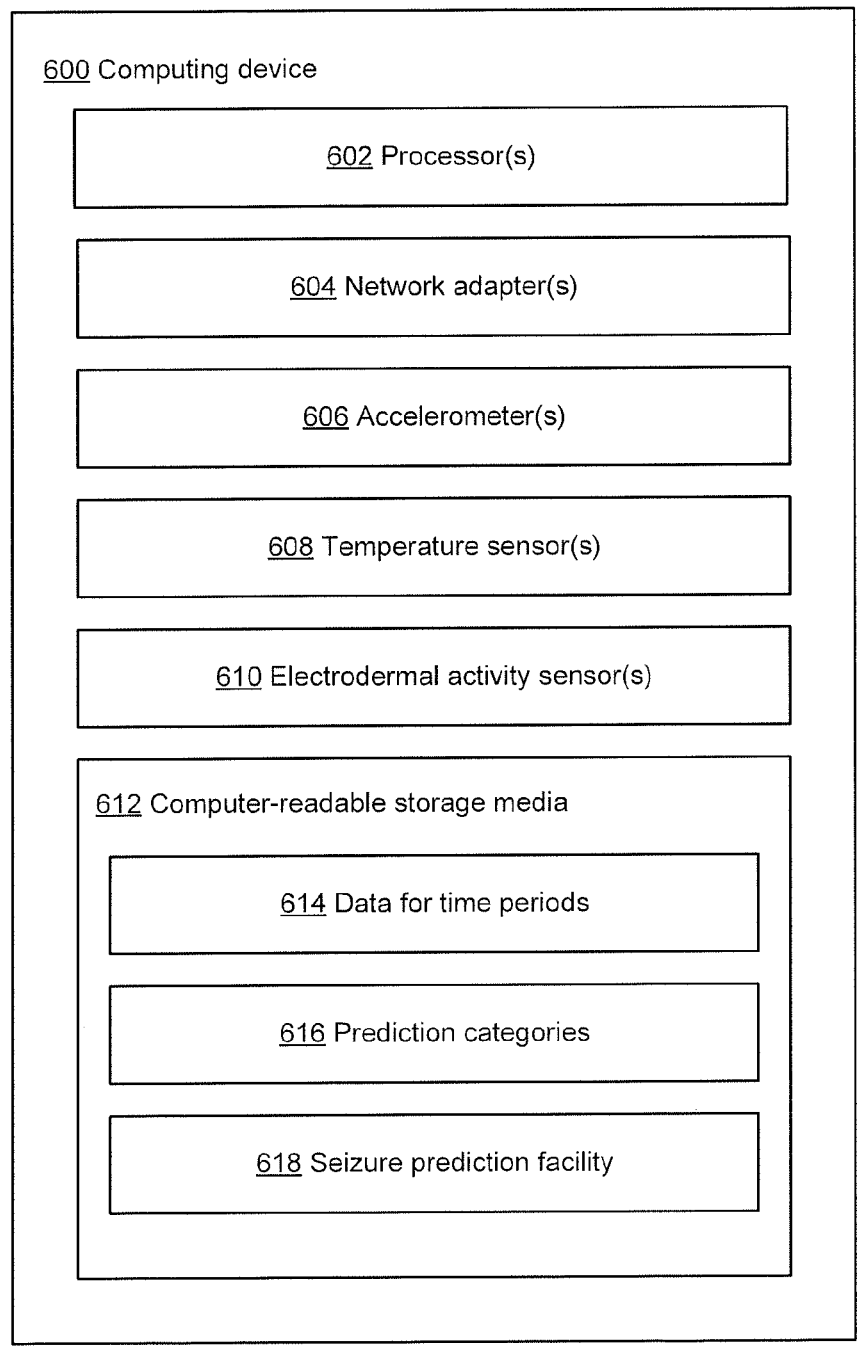
FIG. 6 is a block diagram of an example of a computing device with which some embodiments may operate.

FIG. 6 illustrates one exemplary implementation of a computing device in the form of a computing device 600 that may be used in a system implementing techniques described herein, although others are possible. Computing device 600 may, for example, be implemented as a wearable device, such as device 104 of FIG. 1. It should be appreciated that FIG. 6 is intended neither to be a depiction of necessary components for a computing device to operate as a wearable device 104 or any other computing device of a system operating according to techniques described herein, nor a comprehensive depiction.

Computing device 600 may comprise at least one processor 602, a network adapter 604, and computer-readable storage media 612. Computing device 600 may be, for example, a wearable device, a desktop or laptop personal computer, a personal digital assistant (PDA), a smart mobile phone, a tablet computer, a server, or any other suitable computing device. Network adapter 604 may be any suitable hardware and/or software to enable the computing device 600 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media 612 may be adapted to store data to be processed and/or instructions to be executed by processor 602. Processor 602 enables processing of data and execution of instructions. The data and instructions may be stored on the computer-readable storage media 612 and may, for example, enable communication between components of the computing device 600.

Device 600 may, in some embodiments (e.g., embodiments in which the device 600 is a wearable device), include one or more sensors to sensor biological characteristics or other data. In the example of FIG. 6, the device 600 includes one or more accelerometers 606, one or more temperature sensors 608, and one or more electrodermal activity (EDA) sensors 610.

The data and instructions stored on computer-readable storage media 612 may comprise computer-executable instructions implementing techniques which operate according to the principles described herein. In the example of FIG. 6, computer-readable storage media 612 stores computer-executable instructions implementing various facilities and storing various information as described above. Computer-readable storage media 612 may store data 614 for one or more time periods, such as biological characteristic data, acceleration data, or other data for time periods. The media 612 may further store data 616 on prediction categories, which may include definitions for each of the prediction categories. The media 612 may additionally store instructions for a seizure prediction facility 618, which may implement any of the techniques described above for predicting occurrence of a seizure during a time period.

While not illustrated in FIG. 6, a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

The word "exemplary" is used herein to mean serving as an example, instance, or illustration. Any embodiment, implementation, process, feature, etc. described herein as exemplary should therefore be understood to be an illustrative example and should not be understood to be a preferred or advantageous example unless otherwise indicated.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the principles described herein. Accordingly, the foregoing description and drawings are by way of example only.

The invention claimed is:

1. An apparatus comprising:
a wrist device arranged to be worn on a wrist of an epilepsy patient, wherein the wrist device comprises:
at least one first sensor configured to measure temperature of the epilepsy patient;
a display;
at least one processor; and
at least one storage having encoded thereon executable instructions that, when executed by the at least one processor, cause the at least one processor to:
receive, using the at least one first sensor, temperature data associated with an epilepsy patient throughout a sleep-wake cycle;
wherein the temperature data comprises a plurality of temperature values during the sleep-wake cycle;
determine a first set of temperature values associated with a first period associated with at least one of a sleep period or a wake period in the sleep-wake cycle;
determine a second set of temperature values associated with a second period associated with at least one of the sleep period or the wake period in the sleep-wake cycle;
determine an autonomic nervous system (ANS) variability value representing a relationship in ANS activity between the sleep period and the wake period associated with the sleep-wake cycle based at least in part on a statistical comparison of the first set of temperature values and the second set of temperature values;
utilize a seizure prediction machine learning neural network to generate a seizure probability score based at least in part on the ANS variability value;
wherein the seizure probability score represents a predicted likelihood of a seizure in a third period associated with a subsequent sleep-wake cycle following the second period based at least in part on the ANS variability value;
wherein the seizure prediction machine learning neural network is trained to model a correlation between:
the relationship in the ANS activity between the sleep period and the wake period, and
a likelihood of a seizure in the epilepsy patient during a next period; and
instruct the display to render a user interface to present a qualitative seizure likelihood prediction representative of the seizure probability score to warn the epilepsy patient of a seizure risk during the third period of the subsequent sleep-wake cycle.

2. The apparatus of claim 1, wherein:
the first period is a wake period during which the patient is awake;
the second period is a sleep period succeeding the wake period and during which the patient is asleep; and
generating the seizure probability score comprises a prediction of whether the patient will experience a seizure in a second wake period and/or a second sleep period succeeding the sleep period.

3. The apparatus of claim 2, wherein:
the apparatus is wearable by the epilepsy patient;
the apparatus further comprises at least one accelerometer; and
the method further comprises:
analyzing movement information generated by the at least one accelerometer to identify the wake period; and
analyzing movement information generated by the at least one accelerometer to identify the sleep period.

4. The apparatus of claim 1, wherein determining the ANS variability value comprises calculating a ratio of a first statistical value representing the first set of temperature values to a second statistical value representing the second set temperature values.

5. The apparatus of claim 4, wherein calculating the ratio comprises:
calculating the first statistical value for the first temperature based at least in part on a statistical value calculation of the first set of temperature values;
calculating the second statistical value for the second temperature based at least in part on a statistical value calculation of the second set temperature values; and
calculating the ratio of the second statistical value to the first statistical value.

6. The apparatus of claim 5, wherein:
calculating the first statistical value comprises calculating an average temperature for the first period; and
calculating the second statistical value comprises calculating an average temperature for the second period.

7. The apparatus of claim 5, wherein generating the seizure probability score comprises:
comparing the ratio to a definition of one or more categories of prediction; and
in response to determining that the ratio satisfies a definition of a category of the one or more categories, outputting a prediction associated with the category.

8. The apparatus of claim 7, the method further comprises:
analyzing temperature data associated with one or more patients over time to determine the definition.

9. The apparatus of claim 8, wherein the one or more patients includes the epilepsy patient.

10. The apparatus of claim 8, wherein analyzing temperature data associated with one or more patients over time to determine the definition comprises using a machine learning process.

11. The apparatus of claim 7, wherein comparing the ratio to a definition of a category comprises comparing the ratio to a threshold associated with the category.

12. The apparatus of claim 1, wherein:
the apparatus further comprises at least one second sensor to sense electrodermal activity;
the method further comprises:
monitoring, using the at least one second sensor and during the first period of time, first electrodermal activity data over the first period to record at least one first electrodermal activity value associated with the first period of time;
monitoring, using the at least one second sensor and during the second period of time, second electrodermal activity data over the second period to record at least one second electrodermal activity value associated with the first period;
determining a second statistical comparison value representing a statistical comparison of the at least one first electrodermal activity value with the at least one second electrodermal activity value; and
generating the seizure probability score using the seizure prediction machine learning neural network trained to predict the likelihood of the seizure in the third period following the second period based at least in part on the statistical comparison value and the second statistical comparison value.

13. The apparatus of claim 12, wherein:
comparing the first electrodermal activity data over the first period of time to the second electrodermal activity data over the second period of time comprises calculating a second ratio of a second electrodermal activity statistical value representing the at least one second electrodermal activity value to a first electrodermal activity statistical value representing the at least one first electrodermal activity value; and
calculating the second ratio comprises:
calculating the first electrodermal activity statistical value for the first electrodermal activity of the patient over the first period;
calculating the second electrodermal activity statistical value for the second electrodermal activity of the patient over the second period; and
calculating the second ratio of the second electrodermal activity statistical value to the first electrodermal activity statistical value.

14. The apparatus of claim 13, wherein generating the prediction based at least in part on the ANS variability value comprises comparing the ratio of the second electrodermal activity statistical value to the first electrodermal activity statistical value to one or more thresholds.

15. The apparatus of claim 1, wherein:
the first period is a period extending for more than two hours and less than 24 hours;
the second period is a period extending for more than two hours and less than 24 hours and that immediately follows the first period; and
wherein the seizure probability score comprises a prediction that the patient will experience a seizure during the third period immediately following the second period, the third period being a period extending for more than two hours and less than 24 hours.

16. A system to predict occurrence of a seizure in a monitored individual, the system comprising:
a wrist device arranged to be worn on a wrist of the monitored individual, wherein the wrist device comprises an accelerometer to measure a movement, a temperature sensor to sense temperature, and an electrodermal activity (EDA) sensor to sense EDA, the wrist device further comprising a display to render a user interface to output diagnostic information for the monitored individual;
wherein the monitored individual comprises an epileptic patient;
at least one processor; and
at least one storage medium having encoded thereon executable instructions that, when executed by the at least one processor, cause the at least one processor to carry out a method comprising:
determining, based on acceleration data collected by the accelerometer, a wake period of a sleep-wake cycle during which the monitored individual is awake;
receiving, using the temperature sensor and during the wake period, first temperature data over the wake period comprising a first set of temperature values;
receiving, using the EDA sensor and during the wake period, first EDA data over the wake period comprising a first set of EDA values;
determining, based on acceleration data for the wrist of the monitored individual collected by the accelerometer, a sleep period of the sleep-wake cycle during which the monitored individual is asleep;
receiving, using the temperature sensor and during the sleep period, second temperature data over the sleep period comprising a second set of temperature values;
receiving, using the EDA sensor and during the sleep period, second EDA data over the wake period comprising a second set of EDA values;
determining an autonomic nervous system (ANS) variability value representing a relationship in ANS activity between the sleep period and the wake period associated with the sleep-wake cycle based at least in part on a statistical comparison between:
  i) the first set of temperature values and the second set of temperature values, and
  ii) the first set of EDA values and the set of EDA values;
utilizing a seizure prediction machine learning neural network to generate a seizure probability score based at least in part on the ANS variability value;

wherein the seizure probability score represents a predicted likelihood that the monitored individual will experience a seizure during a second wake period following the sleep period based at least in part on the ANS variability value;

wherein the seizure prediction machine learning neural network is trained to model a correlation between:

the relationship in the ANS activity between the sleep period and the wake period, and a likelihood of a seizure in the epilepsy patient during a next period; and instructing the display to render a user interface to present a qualitative seizure likelihood prediction representative of the seizure probability score to warn the monitored individual of a seizure risk during the second wake period.

17. The system of claim 16, wherein the at least one processor and the at least one storage medium are disposed in the wrist device.

18. The system of claim 16, wherein the at least one processor and the at least one storage medium are disposed in a computing device physically separate from the wrist device.

19. A method comprising:

receiving throughout a sleep-wake cycle from at least one first sensor configured to measure temperature, by at least one processor, temperature data comprising a plurality of temperature values associated with an epilepsy patient;

wherein the at least one first sensor is positioned in a wrist device configured to be worn on a wrist of the epilepsy patient determining, by at least one processor, first set of temperature values associated with a first period of a sleep period and a wake period in a sleep-wake cycle;

determining, by the at least one processor, second set of temperature values associated with a second period of the sleep period and a wake period in the sleep-wake cycle, the second period following the first period in the sleep-wake cycle;

determining, by the at least one processor, an autonomic nervous system (ANS) variability value representing a relationship in ANS activity between the sleep period and the wake period associated with the sleep-wake cycle based at least in part on a statistical comparison of the first set of temperature values and the second set of temperature values;

utilizing, by the at least one processor, a seizure prediction machine learning neural network to generate a seizure probability score based at least in part on the ANS variability value;

wherein the seizure probability score represents a predicted likelihood of a seizure in a third period associated with a subsequent sleep-wake cycle following the second period based at least in part on the ANS variability value;

wherein the seizure prediction machine learning neural network is trained to model a correlation between:

the relationship in the ANS activity between the sleep period and the wake period, and a likelihood of a seizure in the epilepsy patient during a next period; and instructing, by the at least one processor, the display to render a user interface to present a qualitative seizure likelihood prediction representative of the seizure probability score to warn the epilepsy patient of a seizure risk during the third period of the subsequent sleep-wake cycle.

20. The method of claim 19, wherein comparing the first set of temperature values over the first period of time to the second set of temperature values over the second period of time comprises calculating a ratio of a second statistical value representing the second set of temperature values to a first statistical value representing the first set of temperature values.

* * * * *